(12) United States Patent
Schwarz et al.

(10) Patent No.: US 10,194,136 B2
(45) Date of Patent: Jan. 29, 2019

(54) APPARATUS FOR RECORDING AN IMAGE OF AN OBJECT FIELD ON A HUMAN OR ANIMAL BODY

(71) Applicant: KARL STORZ GmbH & Co. KG, Tuttlingen (DE)

(72) Inventors: Peter Schwarz, Tuttlingen-Nendingen (DE); Christian Graf, Emmingen-Liptingen (DE)

(73) Assignee: KARL STORZ SE & Co. KG, Tuttlingen (DE)

( * ) Notice: Subject to any disclaimer, the term of this patent is extended or adjusted under 35 U.S.C. 154(b) by 332 days.

(21) Appl. No.: 15/079,772

(22) Filed: Mar. 24, 2016

(65) Prior Publication Data

US 2016/0286197 A1    Sep. 29, 2016

(30) Foreign Application Priority Data

Mar. 24, 2015 (DE) .......................... 10 2015 003 681
Mar. 12, 2016 (EP) ...................................... 16000595

(51) Int. Cl.
*A61B 1/04* (2006.01)
*H04N 13/25* (2018.01)
(Continued)

(52) U.S. Cl.
CPC ......... *H04N 13/25* (2018.05); *A61B 1/00096* (2013.01); *A61B 1/00186* (2013.01);
(Continued)

(58) Field of Classification Search
CPC ................ H04N 13/025; A61B 90/361; A61B 1/00096; A61B 1/00186; A61B 1/00193;
(Continued)

(56) References Cited

U.S. PATENT DOCUMENTS 4,597,643 A  *  7/1986  Podvin ................. G02B 26/007
                                               16/223
4,608,622 A  *  8/1986  Gonser ................ A61C 19/003
                                               250/493.1
(Continued)

FOREIGN PATENT DOCUMENTS

DE          199 03 437 C1      8/2000
DE     10 2008 018 636 A1     10/2009
(Continued)

*Primary Examiner* — Christopher G Findley
(74) *Attorney, Agent, or Firm* — Muncy, Geissler, Olds & Lowe, P.C.

(57) ABSTRACT

An apparatus for recording an image of an object field on a body from outside of the body has a shank and an optical unit. The optical unit includes an observation optical unit for recording the image of the object field and is rotatable about an axis of rotation. The observation optical unit has a first stereo channel and a second stereo channel that each has one objective and at least one electronic image recorder. The observation optical unit includes at least one filter that is swivelable into a beam path of the observation optical unit. The at least one filter is swivelable about a swivel axis that is substantially perpendicular to the axis of rotation. At least one filter is swivelable into a beam path of the observation optical unit and into a spatial region arranged laterally with respect to the beam paths of both stereo channels.

21 Claims, 7 Drawing Sheets

(51) Int. Cl.
*A61B 1/00* (2006.01)
*G02B 21/00* (2006.01)
*G02B 23/24* (2006.01)
*A61B 90/00* (2016.01)
*G02B 5/20* (2006.01)
*G02B 27/10* (2006.01)
*A61B 5/00* (2006.01)
*A61B 1/05* (2006.01)
*A61B 90/30* (2016.01)

(52) U.S. Cl.
CPC .......... *A61B 1/00193* (2013.01); *A61B 1/051* (2013.01); *A61B 5/0071* (2013.01); *A61B 5/0077* (2013.01); *A61B 90/361* (2016.02); *G02B 5/208* (2013.01); *G02B 21/0008* (2013.01); *G02B 23/2415* (2013.01); *G02B 27/1013* (2013.01); *A61B 2090/309* (2016.02); *A61B 2090/3616* (2016.02); *A61B 2090/371* (2016.02)

(58) Field of Classification Search
CPC ..... A61B 1/051; A61B 5/0071; A61B 5/0077; G02B 5/208; G02B 21/0008; G02B 23/2415; G02B 27/1013
See application file for complete search history.

(56) References Cited

U.S. PATENT DOCUMENTS

| | | | |
|---|---|---|---|
| RE34,411 E * | 10/1993 | Nishioka | A61B 1/05 348/70 |
| 5,278,639 A * | 1/1994 | Fort | A61B 1/05 348/279 |
| 5,749,830 A * | 5/1998 | Kaneko | A61B 1/00082 348/E5.038 |
| 6,641,531 B2 | 11/2003 | Kehr | |
| 7,649,685 B2 | 1/2010 | Spink | |
| 8,040,599 B2 | 10/2011 | Steffen et al. | |
| 8,262,559 B2 | 9/2012 | Krattiger | |
| 8,337,201 B1 * | 12/2012 | Mace | G02B 5/22 433/29 |
| 8,614,851 B2 | 12/2013 | Kuster | |
| 8,692,912 B2 * | 4/2014 | Fish | H04N 5/2254 348/269 |
| 8,702,602 B2 | 4/2014 | Berci et al. | |
| 9,241,616 B1 * | 1/2016 | Mortensen | G03B 15/14 |
| 9,949,625 B2 * | 4/2018 | Fukuda | A61B 1/0646 |
| 2005/0027166 A1 * | 2/2005 | Matsumoto | A61B 1/041 600/162 |
| 2007/0153542 A1 * | 7/2007 | Gono | A61B 1/0638 362/574 |
| 2012/0248333 A1 | 10/2012 | Fallert et al. | |
| 2015/0010878 A1 * | 1/2015 | Seibel | G01N 21/645 433/27 |
| 2015/0085084 A1 | 3/2015 | Heni et al. | |
| 2015/0085093 A1 | 3/2015 | Heni et al. | |
| 2015/0316479 A1 * | 11/2015 | Thrush | G01N 21/6456 250/458.1 |

FOREIGN PATENT DOCUMENTS

| | | |
|---|---|---|
| DE | 10 2006 004 232 C5 | 8/2013 |
| DE | 10 2013 110 543 A1 | 3/2015 |
| EP | 2 108 306 A1 | 10/2009 |
| EP | 2 505 989 A1 | 10/2012 |
| EP | 2 514 357 A1 | 10/2012 |
| EP | 2 609 849 A1 | 7/2013 |
| EP | 2 850 996 A1 | 3/2015 |
| EP | 2 850 997 A1 | 3/2015 |
| WO | WO 2012/041445 A1 | 4/2012 |

* cited by examiner

APPARATUS FOR RECORDING AN IMAGE OF AN OBJECT FIELD ON A HUMAN OR ANIMAL BODY

This nonprovisional application claims priority under 35 U.S.C. § 119(a) to German Patent Application No. 10 2015 003 681.5, which was filed in Germany on Mar. 24, 2015, and to European Patent Application No. 16000595.5, which was filed in Europe on Mar. 12, 2016, and which are both herein incorporated by reference.

BACKGROUND OF THE INVENTION

Field of the Invention

The present invention relates to an apparatus for recording an image of an object field on a human or animal body.

Description of the Background Art

U.S. Pat. No. 7,649,685 B2 discloses an arrangement for a stereo microscope with an illumination apparatus, the light of which lies in a regulable spectral range. A filter is swiveled or inserted into an observation beam path by means of an electromechanical movement device. Similar electromechanical movement devices are provided for introducing filters into the illumination beam paths. In accordance with U.S. Pat. No. 8,614,851 B2, observation filters can be swiveled or inserted into the observation beam path in a fluorescence operating stereo microscope for the controllable attenuation in the excitation wavelength range.

DE 10 2006 004 232 C5, which corresponds to U.S. Pat. No. 8,040,599, discloses a microscopy system for observing fluorescences of various fluorescent dyes in an object plane, wherein the microscopy system comprises an illumination system and an observation system. A first observation filter carrier and a second observation filter carrier, which are embodied as a rotatably mounted aluminum disk in each case, are respectively arranged in a first observation beam path and a second observation beam path for optical imaging of the object, carry two different transmission filters in each case and have an opening. By means of two drives, the first observation filter carrier and the second observation filter carrier can each be rotated about an axis parallel to the optical axis of the relevant observation beam path in order to arrange appropriate transmission filters in the first and second observation beam paths in accordance with a respectively selected operating state.

DE 199 03 437 C1, which corresponds to U.S. Pat. No. 6,641,531, which is incorporated herein by reference, discloses an apparatus for swiveling in and out at least one optical component within an endoscopic system. The component can be swivelable into the beam path of the endoscopic system and swivelable out of the beam path again, with the swivel axis being arranged extending at an angle to the optical axis.

EP 2 505 989 A1, which corresponds to US 2012/0248333, which is incorporated herein by reference, provides an apparatus for fluorescence diagnostics an can have an illumination system for illuminating a target region and an observation system for observing the target region in a white-light mode and in a fluorescence mode, wherein the observation system can have at least one first image sensor for receiving a white-light image and at least one second image sensor for receiving a fluorescence image. Assigned to the second image sensor in the observation beam path can be an observation spectral filter, the filter characteristic of which may be designed in such a way that light in the spectral range of fluorescence to be observed can be fed to the second image sensor while light in the spectral ranges outside of the fluorescence may be blocked. The observation system can have a stereo endoscope. Here, the stereo endoscope can have, for example, two optics channels, wherein an image sensor can be arranged in each one of the two optics channels, one of which image sensors serves to receive a fluorescence image, wherein in the observation spectral filter which can be swiveled into the beam path can be assigned to this image sensor.

EP 2 514 357 A1, which corresponds to U.S. Pat. No. 8,702,602, which is incorporated herein by reference, discloses an apparatus for observing and illuminating an object field on a patient from a location outside of the body of the patient, the apparatus can have a lens system for observing the object field in a viewing direction and an illumination for illuminating the object field. The apparatus furthermore can have a shank, at a distal end of which a head part which is widened in comparison with the diameter of the shank can be arranged. The head part can have arranged therein at least one emitting illumination unit for homogeneous illumination of the object field at distances from a few centimeters up to, for example, one meter. Power lines for the at least one illumination unit are arranged in the shank. Furthermore, the shank holds a rod lens system which forwards the image of the operating field to a proximal end of the shank. Such a device can also be referred to as an "exoscope". Exoscopes of the aforementioned type are available from Karl Storz GmbH & Co. Kg under the trade name VITOM®.

EP 2 850 996 A1, which corresponds to US 2015/0085084, which is incorporated herein by reference, discloses an apparatus for recording an image of an object field on a human or animal body from outside of the body. The apparatus comprises a shank and an observation optical unit, arranged at a distal end of the shank, for recording the image of the object field. The observation optical unit can be embodied as a stereo optical unit. As a result of this, an improved spatial perception of the object field is made possible. Since it is not only the image of the operating field generated by an electronic image recorder but also, additionally, the baseline of the stereoscopic optical unit that rotates in the case of a rotation of the shank about an axis approximately parallel to the viewing direction of the optical unit, the observation optical unit can include an optical unit which is rotatable about a first axis of rotation approximately parallel to a viewing direction of the observation optical unit. This renders it possible to depict the recorded stereoscopic image with a substantially unchanged alignment and in such a way that the stereo effect is perceivable for a user or observer, even after swiveling the apparatus.

SUMMARY OF THE INVENTION

It is therefore an object of the present invention to develop a generic apparatus which offers the possibility of recording an image of the object field in different spectral ranges, in particular recording a stereoscopic white-light image and a fluorescence image of the object field, wherein a compact design of the distal end region of the apparatus or of the rotatable optical unit is intended to be made possible at the same time.

In an exemplary embodiment, an apparatus is provided for recording an image of an object field on a human or animal body from a position outside of the human or animal body, which can also be referred to as an "exoscope", and comprises a shank which can have an elongate and rigid embodiment. Alternatively, the shaft can also have a very short embodiment. The object field can be arranged on a surface of the human or animal body or at least partly observable from outside of the body. For example, the object field can be an operating field of a surgical operation. Here, outside can mean that the apparatus can be situated completely outside of the body at all times, for example, also when recording the image of the object field. The apparatus, for example, can have a distance of at least approximately 15 cm, for example in the range from approximately 20 to 75 cm, from the body and can be configured to record the image at a corresponding work distance.

The apparatus according to an embodiment of the invention has an optical unit arranged at a distal end of the shank, the optical unit comprising an observation optical unit for recording the image of the object field and being rotatable relative to the apparatus about an axis of rotation which is at least substantially parallel to a viewing direction of the observation optical unit. In particular, the optical unit is arranged in a head part which is widened in comparison with the diameter of the shank. The observation optical unit can be embodied as a stereo optical unit and comprises a first stereo channel and a second stereo channel, which each can comprise an objective and can each comprise at least one electronic image recorder, wherein the objective in each case can generate an image of the object field on the at least one electronic image recorder assigned to the objective. In particular, the at least one electronic image recorder can be, for example, a semiconductor-based image sensor, for example a CMOS or CCD sensor. The generated image can represent a half image of a stereo image of the object field in each case. The two recorded half images can be displayed to an observer in such a way that the observer obtains a spatial perception of the object field. By way of example, a screen with an alternating polarization can be provided to this end in a manner known per se, with the observer wearing polarization spectacles with different polarizations of the two lenses.

The first stereo channel and the objective of the second stereo channel can be spaced apart from one another in a direction across the viewing direction. The objectives and the image recorders can be arranged within the optical unit. For example, the objectives can be arranged with a fixed spatial relationship with respect to one another, with the distance between the objective of the first stereo channel and the objective of the second stereo channel, measured across the viewing direction, representing the stereo base. With their respective optical axes, the objectives can be arranged parallel to one another or at an angle to one another which is determined by the stereo base and a preferred mean work distance, for example approximately 40 cm. What an angled arrangement can achieve is that the center of each half image of the stereoscopic image represents the same point in the object field at the preferred mean work distance. In the case where the optical axes of the objectives are at an angle to one another, the "viewing direction" of the observation optical unit denotes a mean direction between the optical axes, in particular corresponding to an angle bisector of the optical axis. The first axis of rotation can be directed parallel or substantially parallel to the viewing direction of the observation optical unit or can be only inclined in relation to the viewing direction by no more than such an angle that the point at which the axis of rotation pierces the object field is contained in the stereoscopic half images recorded by the electronic image recorders of the first stereo channel and of the second stereo channel, independently of the rotation of the optical unit about the first axis of rotation. In an embodiment, the axis of rotation can coincide with a center line between the optical axes, for example with the angle bisector.

Received within the shank are supply and signal lines for provisioning the electronic image recorders and for forwarding the recorded images, in particular the recorded half images of the stereo image, to a proximal end region of the shank, where connectors for connecting supply, evaluation and/or display devices may be provided. Furthermore, arranged within the shank there may also be, for example, optical waveguides for forwarding illumination light to the distal end of the shank, where an illumination device for illuminating the object field may be provided. The illumination device can be arranged proximally from the observation optical unit in the distal end region of the apparatus, for example at the head part of the apparatus which is widened in relation to the shank. The exoscope can be held by a holder which has an articulated arm, at the distal end of which there is arranged a gripper, which is embodied for a secure hold of the exoscope, for example for gripping and clamping the shank. By adjusting the holder, the exoscope can be affixed at a suitable distance from the object field and with a suitable position and alignment, depending on the imposed requirements. If the optical unit of the exoscope is embodied as a side-viewing optical unit with a viewing direction that forms an angle of approximately 90° with the longitudinal axis of the shaft, the exoscope can be positioned for observing a horizontally arranged object field which, for example, can be an operating field in the case of a surgical operation on the human body, for example, it can be positioned over the object field with a viewing direction directed perpendicular or substantially perpendicular downward. Depending on the requirements and depending on the side from which an unimpeded access to the operating field is required, the exoscope can be brought in different positions with an approximately unchanging viewing direction by adjusting the holder and, to this end, the exoscope can be swiveled about a vertical axis.

According to an exemplary embodiment of the invention, the observation optical unit can comprise at least one filter, which is embodied, for example, as a transmission filter and which is swivelable into a beam path of the observation optical unit, i.e. into a beam path of at least one of the stereo channels, and swivelable therefrom. Here, the at least one filter is swivelable about a swivel axis directed substantially perpendicular to the axis of rotation. In particular, the at least one filter can be swiveled about a swivel axis directed substantially perpendicular to the viewing direction. The at least one filter can be mounted in a corresponding swivelable manner within the optical unit for the purposes of being swiveled into the beam path and being swiveled out of the beam path, with the swivel axis being defined by the mount. The swivel axis can extend through the optical unit and can be arranged at an unchanging position relative to the optical unit. In the present context, "swiveling in" can denote a swivel or rotational movement of the at least one filter, by means of which the filter is positioned in such a way that all beams, or at least a portion of the beams essential to the image generation, of the relevant beam path pass through the filter. "Swiveling out" can denote a swivel or rotational movement of the filter, as a result of which the filter is arranged in such a way that all beams, or at least a portion of the beams essential to the image generation, of the relevant beam path do not pass through the filter before they reach the relevant image recorder. For example, a respective end position of the movement, which is denoted as "swiveling in" or "swiveling out", is selected in such a way that the radiation incident on the electronic image recorder of the relevant stereo channel is filtered or not filtered, respectively, by the at least one filter; therefore, in this case, the at least one filter is swivelable between a first end position, in which the filter is arranged within the beam path of the observation optical unit, and a second position, in which it is arranged outside of the beam path. The optical unit can comprise further mechanical, optical and/or electronic components.

As a result of the observation optical unit having at least one filter, which is swivelable about a swivel axis substantially perpendicular to the axis of rotation of the optical unit and which, as a result thereof, is introducible into a beam path of at least one of the stereo channels, and removable therefrom again, the selective recording of images of the object field in different spectral ranges can be made possible in a simple manner, with a space-saving arrangement of the at least one filter within the rotatable optical unit being made possible at the same time. For example, this allows a compact construction of the rotatable optical unit such that a likewise space-saving design of the distal end region or of the head part of the apparatus according to the invention is made possible. In particular, the optical unit can be embodied as a compact unit with a substantially cylindrical lateral surface. As a result of this, it is possible to create a stereo exoscope which allows a stereoscopic observation of an object field, for example an operating field in the case of an open surgical operation on the human body, without access of the surgeon to the operating field being substantially restricted, and which exoscope moreover allows the selective observation of the object field in different spectral ranges.

The at least one filter can be embodied in the form of a plane-parallel plate, wherein the swivel axis can lie, for example, in a plane substantially parallel to the surface of the filter. The normal at the surface of the plate-shaped filter can be directed substantially in the direction of the optical axis of the beam path of the relevant stereo channel and, for example, directed substantially parallel to the axis of rotation in the position swiveled into the beam path of the first stereo channel and/or the second stereo channel, while the normal is directed at an angle or substantially perpendicular to the axis of rotation in the swiveled-out position. As a result of this, a reduction of reflection losses and an improved filter effect of the filter, as well as a particularly space-saving arrangement of the filter, are made possible.

In accordance with a preferred embodiment of the invention, the optical axes of the objectives of the first stereo channel and of the second stereo channel lie in a common plane. In the case where the optical axes of the objectives are at an angle to one another, the mean direction between the optical axes, in particular the angle bisector, which defines the viewing direction, also lies in this plane. Preferably, the swivel axis of the at least one filter lies at least approximately in the common plane or in a plane parallel thereto, with the swivel axis advantageously extending through the optical unit in the latter case, for example, past the axis of rotation at a small distance therefrom, or with the swivel axis intersecting the axis of rotation. As a result of this, a further improved use of space is made possible in the case of the swivelable arrangement of the at least one filter within the optical unit.

The observation optical unit can comprise a first filter and a second filter, wherein the first filter is swivelable into the beam path of the first stereo channel and swivelable therefrom again, and the second filter is swivelable into the beam path of the second stereo channel and swivelable therefrom again. As a result of this, a particularly simple design of a stereo optical unit with filters that are introducible into the respective beam paths is created. Further, provision can be made for a single swivelable filter to comprise two filter regions, of which a first filter region is swivelable into the beam path of the first stereo channel and swivelable therefrom again, and a second filter region is swivelable into the beam path of the second stereo channel and swivelable therefrom again. A particularly simple design can also be achieved thereby.

The first filter can be swivelable into the beam path of the first stereo channel between the objective and the at least one image recorder of the first stereo channel and the second filter is swivelable into the beam path of the second stereo channel between the objective and the image recorder of the second stereo channel. This can apply accordingly to the first filter region and the second filter region in accordance with the aforementioned example embodiment. A particularly compact design of the optical unit can be achieved as a result of the respective filter or the respective filter region being introducible between the objective and the image recorder.

The first filter and the second filter can be arranged on a common swivelable filter carrier which can be swivelable about the swivel axis. In particular, the filter carrier can have a U-shaped embodiment, wherein the two outer limbs carry e.g. journals, through which the swivel axis extends, and wherein the central limb is embodied with a plane surface having two windows in which the first filter and the second filter are inserted, through which filters the beam paths of the stereo channels pass through in the swiveled-in position. In the case where a continuous filter is provided with a first filter region and a second filter region in accordance with the aforementioned example embodiment, the filter can be inserted in a window, embodied to be swiveled into the beam paths, of a filter carrier with an otherwise identical design. In this manner, a further simplified and particularly space-saving arrangement is made possible, in which a further improved use of the space available within the optical unit is made possible by the design of the filter carrier and in which, furthermore, the first filter and the second filter are able to be introduced simultaneously into the beam path of the respective stereo channel and are able to be removed therefrom again is easily attainable.

The first filter and the second filter can have substantially the same spectral characteristic, in particular substantially equal spectral transmission functions. For example, the spectral characteristic of the filter can be embodied to observe fluorescence radiation in the same fluorescence mode. By way of example, the first filter and the second filter can therefore both be embodied to observe fluorescence generated by means of protoporphyrin IX or both be embodied to observe just autofluorescence radiation. To this end, the first filter and the second filter can be embodied as described in the European patent application EP 2 505 989 A1, which, as noted above, corresponds to US 2012/0248333. Thus, if the first filter and the second filter are swiveled into the beam paths of the first stereo channel and the second stereo channel, respectively, the apparatus is configured for the stereoscopic observation of the object field in corresponding fluorescence radiation. If the filters are swiveled out, it is possible to record a stereo image of the object field, for example in white light. Instead of a first filter and a second filter, provision can be made for a single filter with a corresponding first filter region and a second filter region.

Alternatively, the first filter and the second filter can have different spectral characteristics, for example, different spectral transmission functions. Thus, for example, the first filter can be embodied to observe induced fluorescence, for example fluorescence induced by protoporphyrin IX, and the second filter can be embodied to observe autofluorescence of the tissue. To this end, the first filter and the second filter can have the aforementioned, but different spectral characteristics. As a result of this, it is rendered possible to observe different fluorescence modes by means of an arrangement with a simple design and to record a stereoscopic image of the object field in white light.

In accordance with an exemplary embodiment of the invention, the at least one filter can be swivelable via a motor in a motor driven manner, i.e., for the purposes of swiveling into the beam path or swiveling out of the beam path of the observation optical unit, the filter is drivable by the motor. In particular, the optical unit comprises a motor-driven drive device, which can comprise an electric motor and gearing, which can be formed of a gear, a plurality of gears, or a gear train, or, for example, which can be embodied with a tractive electromagnet or as an immersion-coil drive. What this renders possible, in particular, is the actuation of the at least one filter from outside of the optical unit for the purposes of introducing the filter into the beam path or for removing the filter from the beam path.

The optical unit can comprise at least one sensor for detecting a swivel position of the at least one filter. This renders it possible to identify the position in which the at least one filter is situated and to monitor the swiveling in and out of the filter.

The at least one sensor can be a magnetic sensor, wherein, for example, a magnet can be connected to the at least one swivelable filter or to the swivelable filter carrier, and the magnetic sensor serving to detect the magnetic field of the magnet can be arranged on a main structure of the rotatable optical unit. It is also possible, for example, to connect the sensor with the at least one swivelable filter or with the swivelable filter carrier and to fasten the magnet to the main structure of the optical unit. This renders monitoring of the swivel movement of the at least one filter possible in a simple manner.

The at least one sensor can be a proximity switch which is arranged and adapted to monitor an end position of the swivel movement of the at least one filter being reached. Such a proximity switch can be a magnetic sensor, for example as described above, or in another way, for example via electrical contacts or as a capacitive proximity sensor. Since, for example, reaching of the end positions of the swivel movement of the at least one filter may be essential for sufficient filtering or an unfiltered passage of the radiation reaching the electronic image recorders, this enables monitoring of the swivel movement in a particularly simple manner.

In accordance with an embodiment of the invention, the observation optical unit can comprises a focusing device. The focusing device can comprise, for example, a guide directed substantially parallel to the optical axis of the objective of the first stereo channel and/or the second stereo channel, along which guide the relevant objective can be displaceable in a motor-driven manner. The objective of the first stereo channel and the objective of the second stereo channel are arranged on a common carriage which is displaceable substantially along the viewing direction of the observation optical unit on at least one guide. What this renders possible is the adaptation of the observation optical unit to different work at distances. Furthermore, this enables refocusing, which may be necessary due to the swiveling of the at least one filter into, or out of, the beam path of the observation optical unit and the change in the optical path length caused thereby. The objectives can be displaceable in a motor driven manner, as a result of which automatic refocusing and/or an actuation of the focusing from outside of the optical unit is made possible.

The optical unit can comprises a marker light source which generates a marker light beam directed substantially parallel to the viewing direction of the observation optical unit. To this end, the optical unit can comprise, for example, a laser or a light-emitting diode (LED) and a corresponding collimator optical unit. The marker light source enables marking of the object field or a portion of the object field. Preferably, the marker light source generates marker light with a wavelength in the visible spectral range but outside of a fluorescence range observable by means of the observation optical unit such that a recorded fluorescence image is not impaired by the marker light. As a result of this, a region in which an image, in particular a fluorescence image, of the object field is recorded becomes easily identifiable for a user of the apparatus.

In accordance with an embodiment of the invention, the first stereo channel and the second stereo channel can each comprise at least one further electronic image recorder, for example, exactly one further electronic image recorder, and a beam splitter, wherein the beam splitter is arranged and adapted to split the radiation that entered into the respective stereo channel between the at least two image recorders of the respective stereo channel. The beam splitters of the first stereo channel and the second stereo channel can, in each case be embodied in a dichroic beam splitting manner such that radiation portions in different wavelength ranges reach the at least two image recorders of the respective stereo channel. Thus, for example, the beam splitter can be embodied in such a way that visible light is reflected onto a first electronic image recorder while infrared light, via transmission, reaches the further electronic image recorder. As a result of this, it may be rendered possible, in particular, to detect fluorescence radiation induced by indocyanine green (ICG) by the further image recorder, while an image in the visible spectral range is recorded by the first image recorder.

The rotatable optical unit can have a hermetically sealed embodiment. To this end, the optical unit can comprise a hermetically sealed housing which has one or more cover glasses inserted into the housing in a hermetically sealed manner on the side facing the object field. For example, the housing can have such a hermetically sealed embodiment that no ingress of vapor into the housing is possible, or at least this cannot occur to any significant extent, even under the temperature and pressure conditions occurring during the sterilization in an autoclave. Therefore, the housing forms a sleeve, by means of which the optical unit is hermetically separated from the surroundings. The housing can have a metallic embodiment, for example, made of a non-ferromagnetic metal. By way of example, aluminum and austenitic steels are suitable therefor. In particular, the objective and the at least one electronic image recorder of the first stereo channel and of the second stereo channel and the at least one swivelable filter and, possibly, a swivelable filter carrier, a drive device of the swivelable filter, a focusing device and/or beam splitter and further electronic image recorders are received within the hermetically sealed housing. Electrical supply and signal lines can be guided through the housing in a sealed manner in order to actuate the image recorders and, optionally, the drives of the filter and/or of the focusing device. In addition or as an alternative to the hermetically sealed embodiment of the optical unit, it is also possible for a housing of the apparatus, for example, a head part of the apparatus, in which the rotatable optical unit is received, and/or an inner housing of the apparatus, which receives the optical components, or else the whole apparatus to have a hermetically sealed embodiment. In this respect, the apparatus can have an embodiment like in the European patent applications EP 14185795.3, which corresponds to US 2015/0085084 and/or EP 14185857.1, which corresponds to US 2015/0085093, and which are both incorporated by reference. This renders it possible in a simple manner to meet the hygienic demands in the case of a use in the sterile region of an operating theater, without substantially restricting the service life of the optical and electronic components contained in the optical unit.

For the manual rotation of the optical unit for erecting the recorded image and for setting the stereo base, provision can be made for a handwheel, for example a rotary cap, which is functionally connected to the rotatably mounted optical unit. Additionally or instead, provision can be made for an electromotive drive for rotating the optical unit. Such a drive for manual or electromotive rotation of the optical unit can be embodied, for example, in accordance with the European patent application EP 14185795.3. However a motor-driven drive for rotating the optical unit can also, for example, comprise an electric motor arranged in the optical unit, which electric motor drives a gearwheel which is mounted in an eccentric fashion in relation to the axis of rotation in the optical unit and which projects beyond an external contour of the optical unit. The gearwheel meshes with a ring gear arranged within the head part of the apparatus and embodied concentrically with respect to the axis of rotation such that an actuation of the electric motor can bring about a rotation of the optical unit about the axis of rotation. A motor-driven drive of the optical unit can enable a particularly simple alignment and an automatic alignment of the stereo optical unit, particularly in the case where a swivel movement of the apparatus is detected by one or more sensors.

The optical unit can be connected in a thermally conducting manner with a heat conductor extending in the shank. This renders possible the dissipation of thermal losses arising during the operation of the electronic image recorders and possible further electrical loads, such as the drives and/or the marker light source. By way of example, provision to this end can be made for a heat pipe extending in the shank to be connected with the distal end thereof to a mount of the optical unit in a thermally conducting manner or for the heat pipe to directly abut an outer side of the optical unit. For example, the optical unit can be mounted on thermally conductive friction bearings, for example made of bronze or graphite foil. Alternatively or additionally, a stripper made of a metallic material, or graphite, can abut an outer surface of the optical unit for dissipating heat. The heat transferred in this manner in the shank can be dissipatable by way of the heat pipe to the proximal end of the shank, where it can be forwarded into the handle and output by way of the surface of the handle. A heat exchanger for further dissipation of the heat to an external cooling device can also be arranged in the proximal end region of the shank or in the handle. Such measures for heat dissipation can also render it possible for the dissipation of thermal losses introduced by an illumination device into the shank and the distal end region thereof.

Also, provision can be made for at least one cable to provide control and/or transfer signals of the electronic image recorders and optional further electric and electronic assemblies which are arranged within the rotatable optical unit. In particular, the cable can be guided within the shank of the apparatus and extend from a proximal end portion of the shank to a distal end portion of the shank, or to a head part arranged at the distal end of the shank. Connectors for establishing a connection to external supply, evaluation and/or indication devices can be provided at the proximal end portion of the shank, or else at a handle connected to the proximal end portion of the shank. By way of example, the cable can be a ribbon cable or as a flexible circuit board and can be wound up on a cylindrical region on the outer side of the optical unit. The distal end region of the exoscope, in particular the head part that is widened in relation to the shank, can have an internal cavity in which a cable reservoir is received, the cable reservoir providing a wound cable portion in the case of a rotation of the optical unit and receiving an unwound cable portion in the case of a rotation of the optical unit in an opposite direction of rotation. In particular, the cable, the cable guide and the cable reservoir can be embodied as described in the European patent application EP 14185857.1.

The apparatus can comprises an illumination optical unit for illuminating the object field. The illumination optical unit can be embodied as described in the European patent application EP 2 514 357 A1. The illumination optical unit of the exoscope can comprise a light source for generating illumination light or it can be connectable to an external light source. The light source can be adapted to selectively generate illumination light with different spectral compositions, for example, for generating illumination light suitable for an observation of the object field in white light and/or in one or more fluorescence modes. Advantageously, the illumination device or the light source can be actuatable synchronously with a drive device of the at least one filter in order, for the observation of at least one fluorescence mode, to control corresponding swiveling in or out of the filter synchronously with the generation of fluorescence excitation radiation suitable therefor. As a result of this, a simple observation of the object field is rendered possible in different spectral ranges, in particular in one or more fluorescence modes.

The observation optical unit can comprise at least one optical filter which, for example, can be a transmission filter which is swivelable into a beam path of the observation optical unit, i.e. into a beam path of at least one of the stereo channels, and swivelable therefrom into a spatial region arranged laterally with respect to the beam paths of both stereo channels. Therefore, a generic apparatus can be embodied as a stereo exoscope with a first stereo channel and a second stereo channel, wherein the two beam paths are arranged adjacent to one another in the optical unit, wherein, for example, the optical axes of the respective objectives can extend in a common plane and wherein a spatial region, in which the at least one filter is arranged when it is swiveled out of the beam path, can be provided laterally next to the two beam paths. This spatial region can be arranged in a direction across a common plane of the optical axes of the objectives and, in a perpendicular or substantially perpendicular projection onto the common plane, it extends over substantially the same extent as the beam paths of the stereo channels. The spatial region can extend within the rotatable optical unit, for example within a cylindrical housing that encloses the beam paths of the stereo channels in a space-saving manner.

What was identified in accordance with the aforementioned further aspect of the invention is that it is possible, in an advantageous manner, to use the space next to the beam paths of the stereo channels, which arise as a result of arranging the beam paths of the two stereo channels of a stereo optical unit next to one another, for receiving the at least one swivelable filter when the latter is swiveled out of the beam path of the observation optical unit. As a result of this, a space-saving design of the distal end region or of the head part of the apparatus according to an embodiment of the invention is made possible, wherein the optical unit can be embodied as a compact unit with a substantially cylindrical lateral surface.

By way of example, the apparatus or the rotatable optical unit can be embodied as described above, wherein the filter, in the swiveled-out position thereof, being arranged in a spatial region arranged laterally with respect to the beam paths of both stereo channels may be attainable by virtue of the at least one filter being swivelable about a swivel axis directed substantially perpendicular to the axis of rotation of the optical unit.

Alternatively, the at least one filter can be swivelable about a swivel axis directed substantially parallel to the axis of rotation, wherein the filter being swivelable out of the beam path of at least one of the stereo channels into a spatial region arranged laterally with respect to the beam paths of both stereo channels may be likewise attainable thereby. In particular, to this end, a swivel axis of the at least one filter can be arranged in a region between the beam paths of the stereo channels or in such a way that the distance of the swivel axis from the axis of rotation is less than the distance of the optical axes of the beam paths of the stereo channels from the axis of rotation, which may coincide with a center line between the two optical axes. This also enables a space-saving arrangement of the swivelable filter, and hence a compact design of the optical unit, in particular with a substantially cylindrical lateral surface.

The optical unit can comprise a first filter and a second filter, wherein the first filter is swivelable into a beam path of the first stereo channel and swivelable therefrom, and the second filter is swivelable into a beam path of the second stereo channel and swivelable therefrom, and wherein, in relation to the axis of rotation, the first filter is offset in the axial direction in relation to the second filter. Further preferably, the first filter can be swivelable about a first swivel axis directed substantially parallel to the axis of rotation and the second filter can be swivelable about a second swivel axis adjacent to the first swivel axis and likewise substantially parallel to the axis of rotation. As a result of this, a particularly space-saving arrangement can be attainable. Otherwise, the apparatus or the optical unit can be embodied as described above.

In accordance with a method according to an embodiment of the invention for recording an image of an object field on a human or animal body from outside of the body, an apparatus, which can be embodied as described above, can be held in an observation position outside of the body, for example by means of a gripper on an articulated adjustable arm of a corresponding holder. In the observation position, the object field is arranged at a work distance in the viewing direction of the apparatus, in particular at a distance from at least approximately 15 cm from the apparatus, for example at a distance in the range from approximately 20 to 75 cm. The apparatus can be situated completely outside of the body at all times, in particular also when recording the image of the object field. In accordance with the method according to the invention, the optical unit with the observation optical unit can be rotated manually and/or in a motor-driven manner about the axis of rotation of the optical unit for the purposes of aligning a stereo base of the stereo optical unit. Furthermore, in accordance with the method according to the invention, at least one filter received in the optical unit can be swiveled into a beam path of the observation optical unit, i.e. of at least one stereo channel, and an image of the object field is recorded by means of the at least one electronic image recorder, that is to say the image recorder of the at least one stereo channel, in a first spectral range which, in particular, is determined by the transmission function of the swiveled-in filter and by a first spectral composition of the illumination light. To the extent that one or more corresponding filters are swiveled into the first stereo channel and the second stereo channel, the recorded image can be a stereo image in the first spectral range. Furthermore, the at least one filter can be swiveled out of the beam path of the observation optical unit into a spatial region, arranged laterally with respect to the beam paths of both stereo channels, within the optical unit and a stereo image of the object field is recorded by means of the respectively at least one electronic image recorder of the first stereo channel and of the second stereo channel in a second spectral range which, in particular, is determined by a second spectral composition of the illumination light. The first spectral composition of the illumination light can be suitable for exciting fluorescence radiation, which is observed by means of the at least one swiveled-in filter, and the second spectral composition can be e.g. white light. As a result of the at least one filter being swiveled out into a spatial region within the optical unit arranged laterally with respect to the beam paths of both stereo channels, a compact design of the rotatable optical unit and hence a design of the distal end region of the apparatus which does not substantially restrict the access to the object field can be made possible. In particular, the swivel axis, about which the at least one filter is swiveled in and out, can be directed substantially perpendicular to the axis of rotation of the optical unit or substantially parallel to the axis of rotation of the optical unit.

Further scope of applicability of the present invention will become apparent from the detailed description given hereinafter. However, it should be understood that the detailed description and specific examples, while indicating exemplary embodiments of the invention, are given by way of illustration only, since various changes, combinations, and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein:

FIGS. 1a and 1b show an exemplary embodiment of an apparatus according to the invention, wherein FIG. 1b is a partly transparent illustration;

DETAILED DESCRIPTION

Figure 1A:
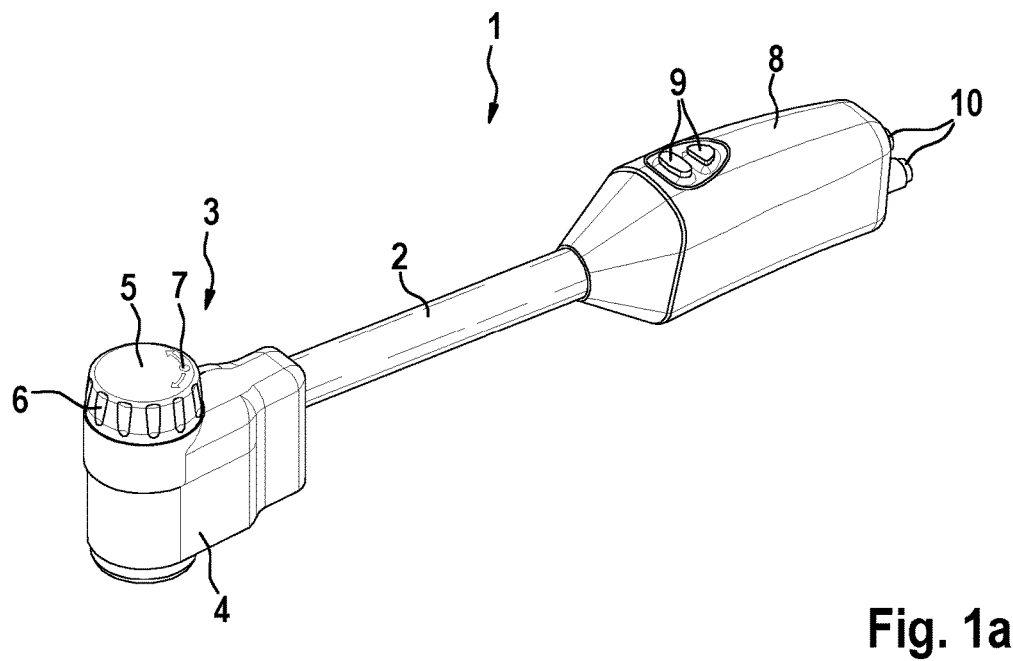
Figure 1B:
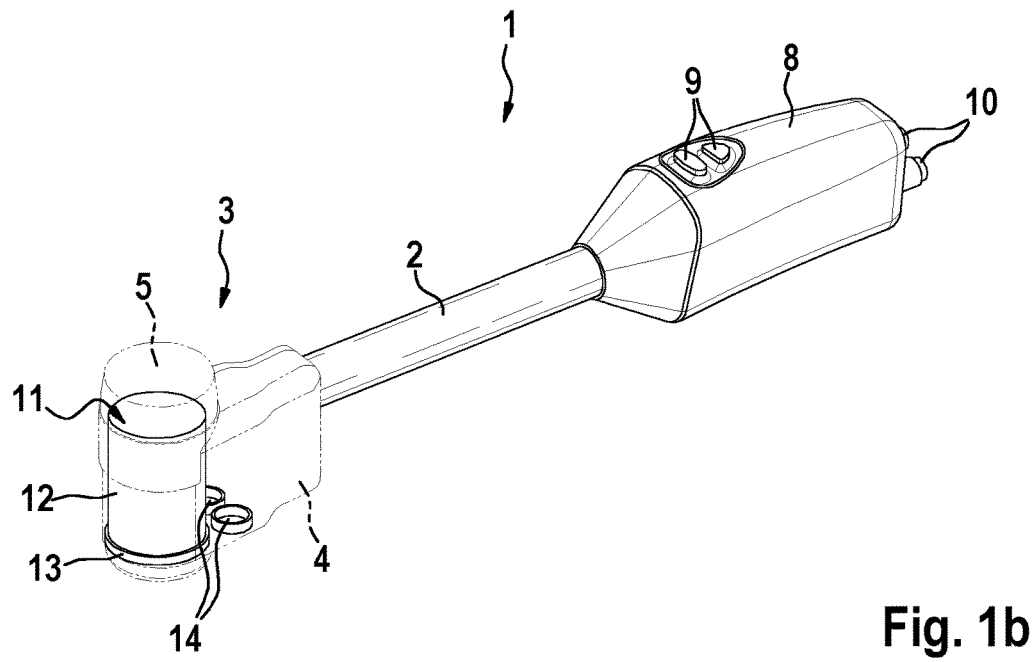

A device according to an exemplary embodiment of the invention, which may be referred to as exoscope 1 below, is shown in a perspective view in FIGS. 1a and 1b. The exoscope 1 has a cylindrical shank 2, at the distal end of which a head part 3, which is widened in comparison with the shank 2, is arranged. The head part 3 has an external housing 4, the distal region of which has an approximately half cylindrical form, wherein the axis of the half cylinder is at an angle of approximately 90° with respect to the longitudinal axis of the shank 2. A rotational cap 5 is placed on the approximately half cylindrical distal end region of the external housing 4, which rotational cap, on the circumferential side thereof, has a plurality of recessed grips 6. Furthermore, on the upper side thereof, the rotational cap 5 has a mark 7 which makes the rotational position of the rotational cap 5 easily identifiable. As indicated by the arrows of the mark 7, the rotational cap 5 is rotatable manually in order to rotate a rotatable optical unit, arranged within the interior of the external housing 4, about an axis of rotation perpendicular to the longitudinal axis of the shank 2. The rotatable optical unit 11 is identifiable in the illustration of FIG. 1b, in which the external housing 4 and the rotational cap 5 are depicted in a transparent manner. The optical unit 11 has a substantially cylindrical embodiment, wherein the axis of the cylinder coincides with the axis of rotation about which the optical unit 11 can be rotated by means of the rotational cap 5. Furthermore, FIG. 1b indicates illumination windows 14 arranged on the lower side of the external housing 4, by means of which illumination windows illumination light is emitted in the direction of an object field to be observed. Furthermore, the exoscope 1 has a handle 8, which is arranged at the proximal end of the shank 2 opposite to the head part 3 and which carries operating elements 9 and connections 10 for electrical signal and supply lines and for an optical fiber for supplying illumination light.

Figure 2:
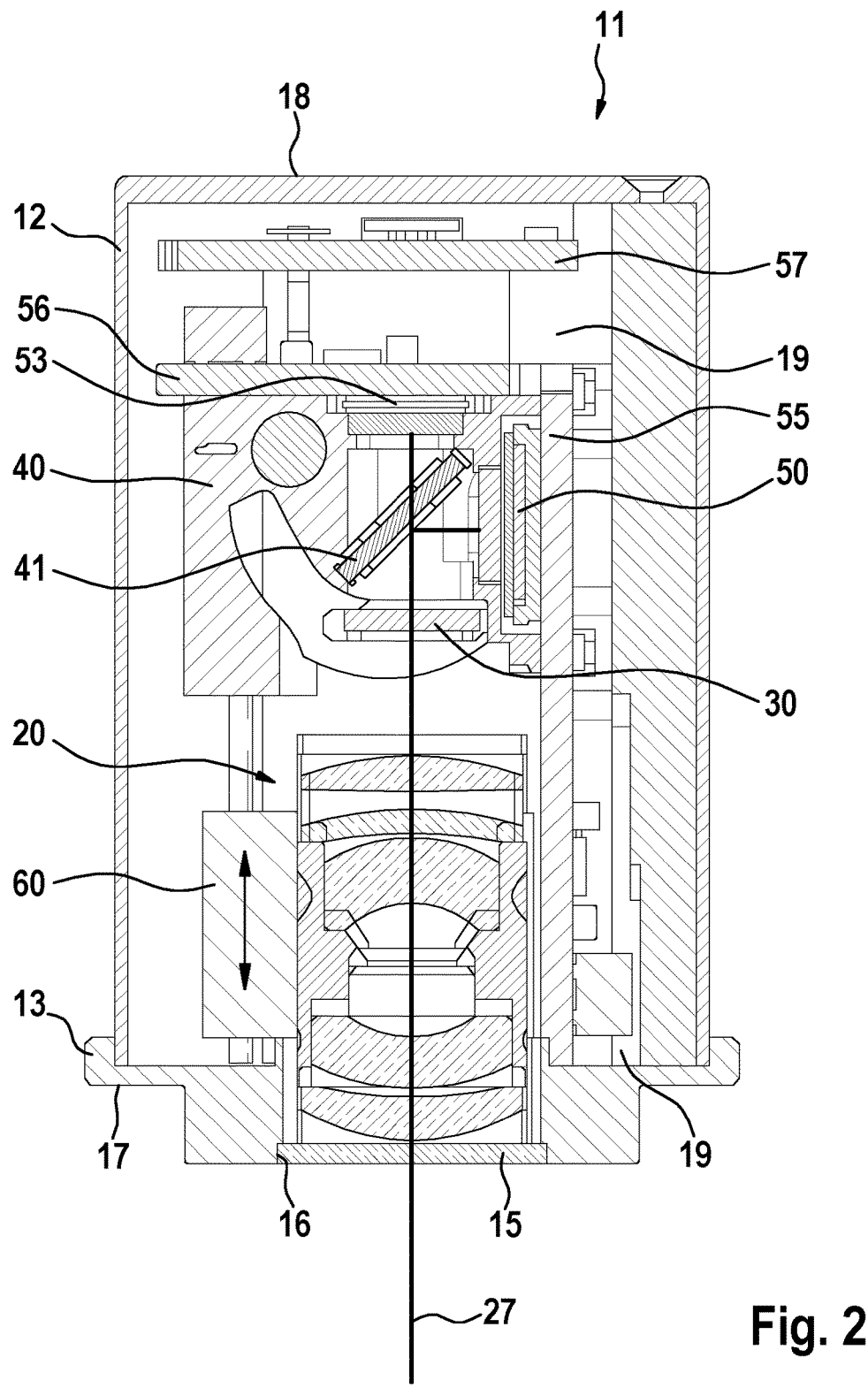
FIG. 2 shows an optical unit in accordance with a first exemplary embodiment of the invention.

FIG. 2 shows a schematic longitudinal section of the rotatable optical unit 11. The optical unit 11 can have a hermetically sealed embodiment, for the purposes of which a substantially cylindrical housing upper part 12 is connected in a sealed manner with the base plate 13 and a cover glass 15 inserted into a recess 16 in the base plate 13 can be inserted in a hermetically sealed manner. Alternatively or additionally, the external housing 4 or the head part 3 of the exoscope 1 or the exoscope 1 overall, i.e. including the shank 2 and the handle 8 (see FIGS. 1a and 1 b), can have a hermetically sealed embodiment. The cover glass 15 can also be embodied as an optical filter or it can be dispensed with, particularly in the case where at least the external housing 4 is hermetically sealed. A step-shaped shoulder 17 of the base plate 13 serves as a bearing face of the rotatable optical unit 11 in the head part 4 (see FIGS. 1a, 1b), just like the upper side 18 of the housing upper part 12. The shoulder 17, the upper side 18 and the remaining regions of the external sides of the housing upper part 12 and of the base plate 13 serve to dissipate heat losses arising within the optical unit 11.

The observation optical unit of the exoscope 1, of which one of the two stereo channels is depicted in FIG. 2, is arranged within the housing of the optical unit 11 formed by the housing upper part 12, the base plate 13 and the cover glass 15. The individual subsystems of the observation optical unit are depicted in detail in FIGS. 3 to 5c and are described below with reference to the aforementioned figures.

Figure 3:
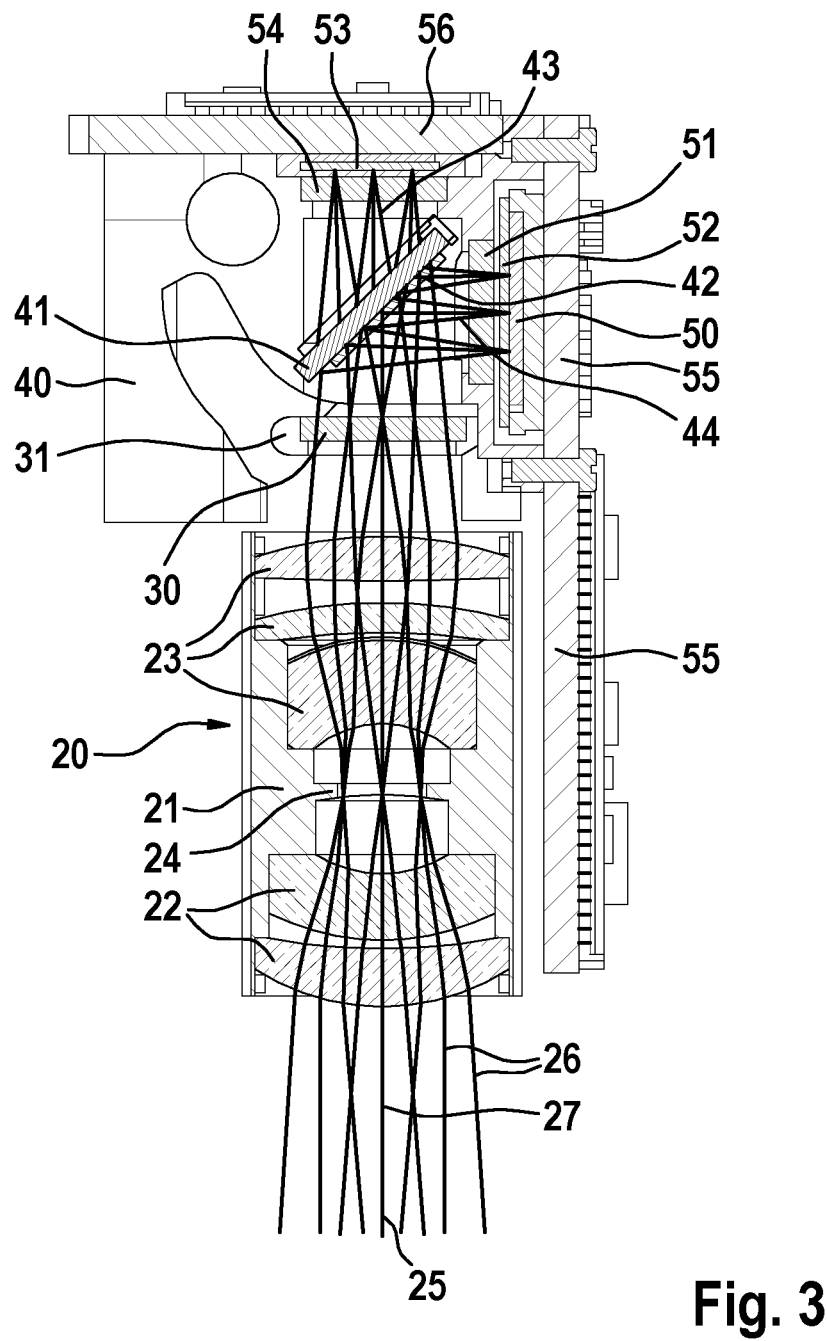
FIG. 3 shows a longitudinal section of a stereo channel of the optical unit in accordance with FIG. 2.

The stereo channel depicted in FIGS. 2 and 3 comprises an objective 20, which has an objective housing 21 acting as a mount for the optical components in the objective 20, in particular for the lenses 22, 23, and furthermore carrying an objective stop 24. The objective 20 has a substantially cylindrical embodiment, wherein the cylinder axis coincides with the optical axis 25 of the objective 20. The optical axis 25 is directed to the object field when observing an object field with the exoscope 1. In FIG. 3, the beam path through the objective 20 is illustrated on the basis of some beams 26 incident from the object field; in FIG. 2, the beam path is merely indicated symbolically by a central beam 27, which coincides with the optical axis 25.

FIGS. 2 and 3 show that an optical filter 30 is swiveled into the beam path of the depicted stereo channel after the objective 20, which filter can, in particular, be a transmission filter, the spectral characteristic of which is adapted to the observation of fluorescence radiation. The filter 30 is embodied as a plane-parallel plate which, in the position shown in FIGS. 2 and 3, is perpendicular to the optical axis 25 of the objective 20. The filter 30 is held in a filter carrier 31, which is mounted in a carrier 40 of the optical unit 11 in a manner swivelable about a swivel axis perpendicular to the optical axis 25 and perpendicular to the plane of the drawing in FIGS. 2 and 3.

The carrier 40 furthermore holds a beam splitter 41 at an angle of approximately 45° with respect to the optical axis 25 of the objective 20. The beam splitter 41 is embodied as a plane-parallel plate with a dichroic beam splitting coating 42 such that beams 26 coming from the object field, after passing through the objective 20 and the filter 30, are divided into a transmitted beam 43 and a reflected beam 44 which have spectrally different compositions. Here, the dichroic beam splitting properties of the coating 42 are selected in such a way that radiation portions in the visible spectral range reach the reflected beam 44 while infrared spectral components form the transmitted beam 43. The reflected beams 44 are incident on an image sensor 50, for example a CMOS or CCD sensor, which serves as an electronic image recorder for recording an image of the object field in the visible spectral range. The sensor area of the image sensor 50 is arranged in an image plane of the objective 20. In particular, the image sensor 50 is sensitive over the whole visible spectral range and therefore records a white-light image of the object field in the case where the object field is illuminated by broadband illumination radiation and the filter 30 is swiveled out of the beam path. In order to avoid the white-light image recorded by the image sensor 50 being interfered with by residual infrared components possibly reaching into the reflected beam path, an infrared cutoff filter 51 is disposed upstream of the image sensor 50, the infrared cutoff filter being fastened to the carrier 40, for example by adhesive bonding. A cover plate 52 is provided in front of the image sensor 50 for protecting the latter. A further electronic image recorder, namely an image sensor 53 with the sensor area thereof arranged in an image plane of the objective 20, is arranged in the transmitted beam path in order to record an image of the object field in the infrared spectral range. The further electronic image recorder or the further image sensor 53 can likewise be a CMOS or CCD sensor. An ICG filter 54, the spectral transmission of which is designed for observing ICG-induced fluorescence, can be arranged in front of the further image sensor 53.

The image sensor 50 and the further image sensor 53 are each arranged on a circuit boards 55, 56 which contain electronic components and circuits for provisioning and controlling the image sensors 50, 53 and for signal processing and signal transmission. As shown in FIG. 2, one or more further circuit boards 57 with further electronic components can be provided in the optical unit 11.

The spectral characteristic of the filters used in the optical unit 11 and in a light source generating the illumination light for illuminating the object field can be selected, for example, in the manner described in the European patent application EP 2 505 989 A1, which is incorporated by reference, or in the European patent application EP 2 609 849 A1, which is incorporated in this respect by reference. In particular, the filters 30, 30' can have a transmission of less than 0.1% in the wavelength range between 380 and 430 nm and a transmission of more than 96% in the wavelength range between 450 and 800 nm for the purposes of observing fluorescence induced by protoporphyrin IX, and they can have a transmission of less than 0.1% in the range from 380 to 455 nm and a transmission of more than 96% in the range from 475 to 800 nm for the purposes of observing autofluorescence. Filters for generating accordingly adapted fluorescence excitation radiation can be provided in the light source. In simple terms, the illumination radiation for exciting the fluorescent dye lies in the region of approximately 405 nm when observing Pp IX fluorescence and the observation of the fluorescence radiation is carried out in the region of approximately 630 nm, while, when observing autofluorescence, the excitation lies in a broad spectral range in the blue region and the observation is carried out in a broadband fashion at wavelengths above approximately 450 nm. The ICG fluorescence can be excited by illumination radiation of approximately 785 nm and it can be observed at wavelengths from approximately 800 to 900 nm; to this end, the ICG filter 54 is transmissive in the last-mentioned wavelength range and preferably only transmissive therein. The illumination radiation for the white-light observation, which takes place in the case of swiveled-out filters 30, 30' and which can take place at the same time as the observation of the ICG fluorescence, can comprise the whole visible spectral range.

Figure 4A:
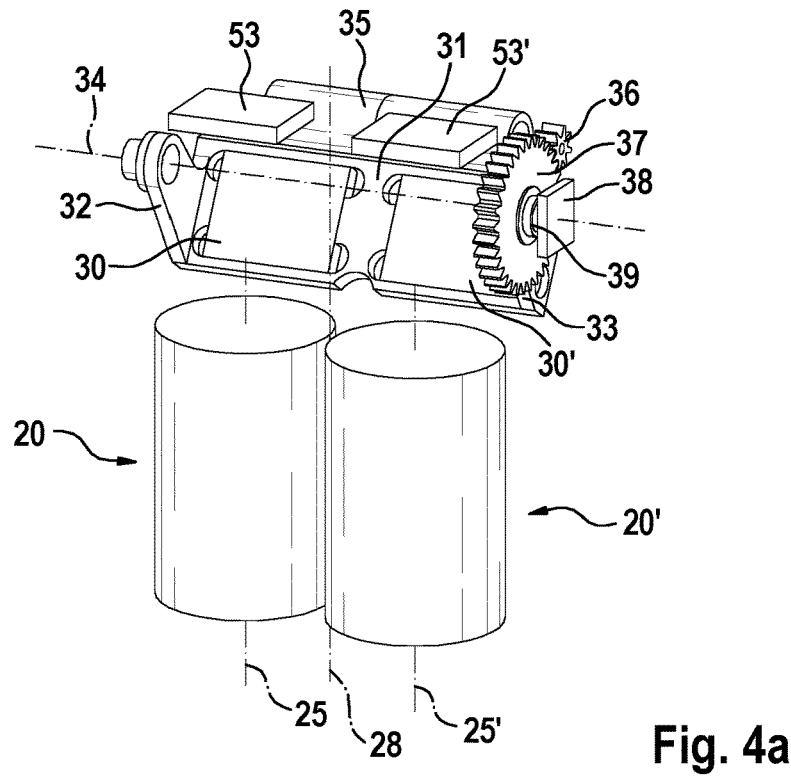
FIGS. 4a and 4b show selected optical elements of the optical unit in accordance with FIG. 2 in a simplified illustration.
Figure 4B:
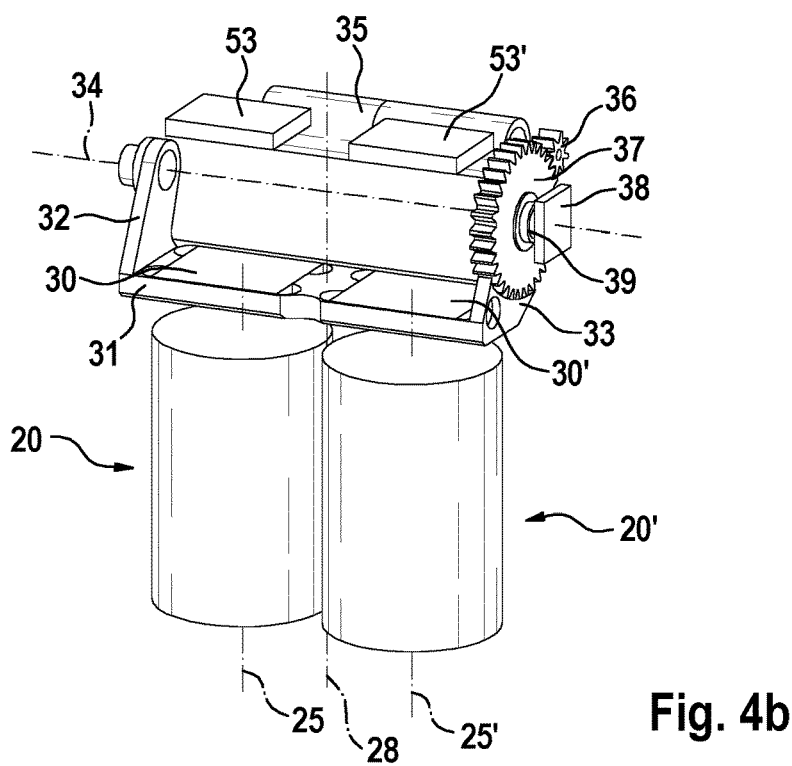

FIGS. 4a and 4b schematically show that a filter 30, 30', swivelable therein, is provided for each one of the two stereo channels of the optical unit 11. As depicted in a simplified form in FIGS. 4a and 4b, the first stereo channel comprises an objective 20 and an image sensor 53, wherein, for reasons of simplicity, only a single image sensor is shown and the beam splitter 41 has not been depicted; however, as shown in FIGS. 2 and 3, a plurality of image sensors 50, 53 and a beam splitter 41 for splitting the observation radiation onto the image sensors 50, 53 can be present. A second stereo channel is formed by the objective 20' and the image sensor 53', wherein two image sensors and a beam splitter may likewise be present in the second stereo channel. The image sensors 53, 53' are each arranged in an image plane of the objective 20, 20'.

The axis of rotation 28 of the optical unit 11 is arranged in the center between the optical axes 25, 25' of the two objectives 20, 20'. The viewing direction coincides with the axis of rotation 28 and it is directed to the object field, i.e. downward in the illustration of FIGS. 4a and 4b. In FIGS. 4a and 4b, the optical axes 25, 25' of the objectives 20, 20' extend parallel to one another; therefore, the axis of rotation 28 is parallel to both optical axes 25, 25'. However, the optical axes 25, 25' of the objectives 20, 20' can also e.g. be at such an angle with respect to one another that the optical axes 25, 25' intersect in the region of a preferred work distance; in this case, the axis of rotation 28 is, in particular, the angle bisector between the two optical axes 25, 25'.

A filter 30, 30' is swivelable in each case into the beam path of the first stereo channel and the second stereo channel between the objective 20, 20' and the respectively assigned image sensor 53, 53'. The two filters 30, 30' are held in a common filter carrier 31. The filter carrier 31 overall has an approximately U-shaped embodiment and it is mounted in a swivelable manner with the ends of the limbs 32, 33 in the carrier 40 of the optical unit 11 (see FIGS. 2, 3) not depicted here. The swivel axis 34 extends perpendicular to the optical axes 25, 25' of the objectives 20, 20' and lies in a plane formed by the optical axes 25, 25'. The swivel axis 34 can intersect the axis of rotation 28 or pass the latter by in the vicinity thereof. As a result of the filter carrier 31 being swivelable about the swivel axis 34, the filters 30, 30' can be swiveled out of the beam paths of the stereo channels and they can be swiveled therein between the objective 20, 20' and the respectively assigned image sensor 53, 53'.

In order to perform the swivel movement, the filter carrier 31 is connected to a drive device, which comprises an electric motor 35 and a first gearwheel 36 fastened to the motor shaft of the electric motor 35, and to a second gearwheel 37, which meshes with the first gearwheel 36 and is connected to the filter carrier 31 or the limb 33. By way of example, the electric motor 35 can be a stepper motor. A swivel movement of the filter carrier 31 in a desired direction can be performed by actuating the electric motor 35. A magnetic sensor 38, which interacts with a magnet 39 connected to the gearwheel 37, is provided for detecting a swivel position of the filter carrier 31.

Figure 5A:
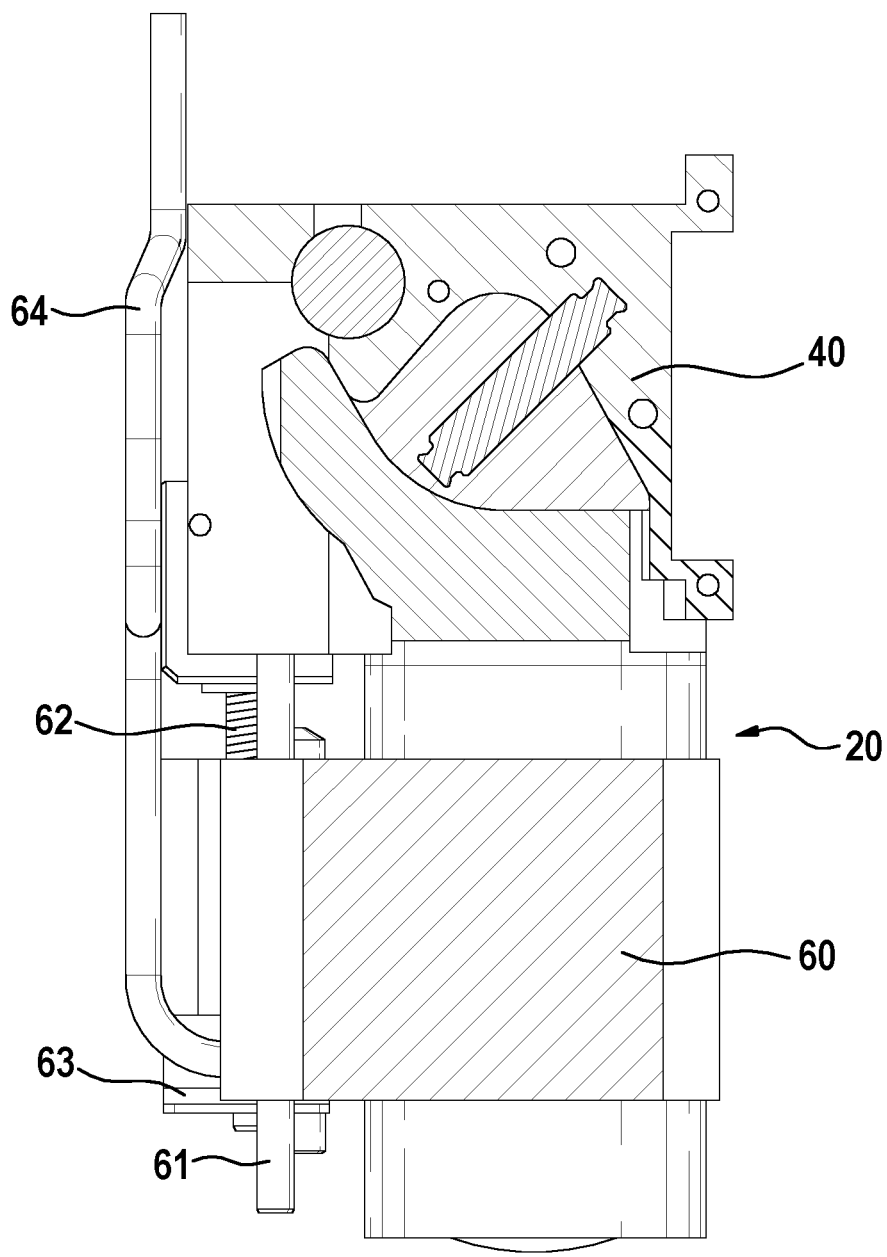
FIGS. 5a to 5c show a focusing device of an optical unit in accordance with FIG. 2 in three different views.
Figure 5B:
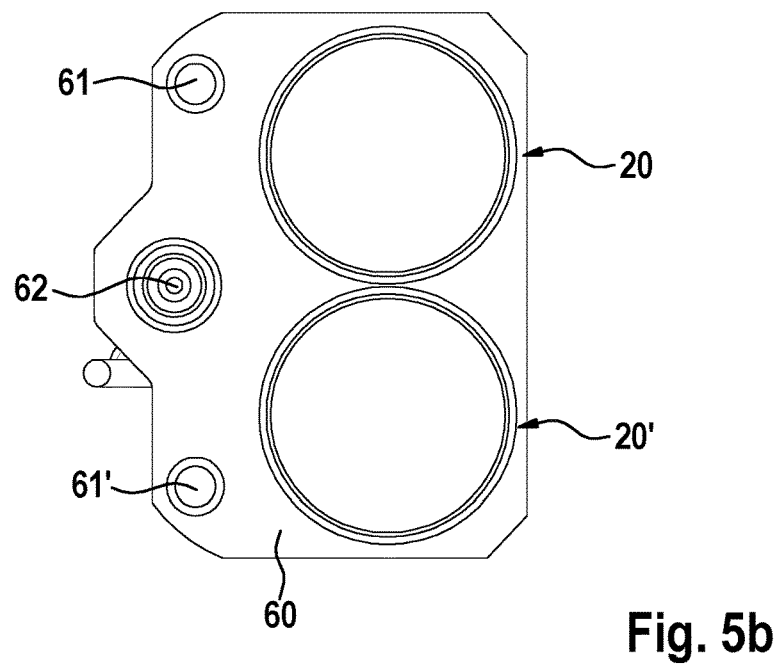
Figure 5C:
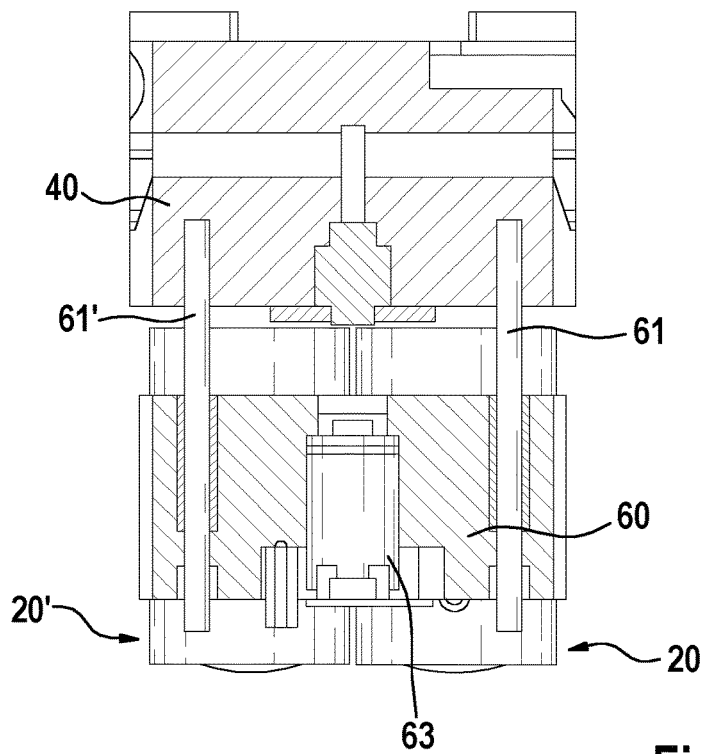

FIGS. 5a to 5c depict a focusing device which serves for refocusing when swiveling the filters 30, 30' into, and out of, the respective beam path and for an adaptation to different work distances from the observed object field. In FIG. 5a, the objective 20 and the carrier 40 of the optical unit 11 are depicted in a view corresponding to that in FIGS. 2 and 3; here, the optical components are not shown for reasons of clarity. What is possible to identify in FIG. 5a is that the objective 20 is received in a carriage 60 which is displaceable in the axial direction, guided on a sliding guide 61 and displaceable by means of a threaded spindle 62. The sliding guide 61 and the threaded spindle 62 are fastened to the carrier 40. A stepper motor 63 is connected to the carriage 60 and it drives a spindle nut (not depicted here) of the threaded spindle 62 in order to displace the carriage 60 along the sliding guide 61. Furthermore, FIG. 5a schematically depicts a cable 64 which serves for provisioning the stepper motor 63. As is possible to identify in the view seen in the axial direction from the object field, as shown in FIG. 5b, the carriage 60 is guided by two sliding guides 61, 61'. The carriage 60 is displaceable on the sliding guides 61, 61' with slide bushings made of e.g. brass, plastic or any other suitable material. As a result of two sliding guides 61, 61' with in each case a long slide bushing or two axially spaced apart shorter slide bushings being provided, the carriage 60 is mounted in a statically overdetermined manner across the axial direction; as a result of this, it is possible to avoid a displacement of the objectives 20, 20' in a transverse direction and an unwanted rotation of the objectives 20, 20' relative to the carrier 40. The spindle nut is mounted on the carriage 60 across the axial direction with a free fit.

Figure 6:
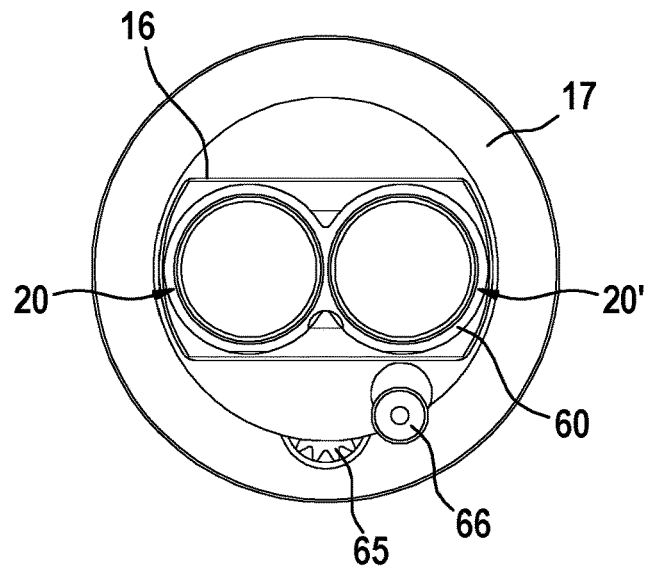
FIG. 6 shows an optical unit in accordance with FIG. 2, as seen against the viewing direction.

FIG. 6 shows the rotatable optical unit in a view corresponding to the view of FIG. 5b. What can be identified from FIG. 6 is that the objectives 20, 20' of the two stereo channels are received next to one another in the carriage 60, which is visible through the recess 16 of the base plate 13. A cover glass 15 (not depicted here) is inserted into the recess 16. Furthermore, the shoulder 17 of the base plate 13, serving as a bearing surface and for heat dissipation, and a gearwheel 65 fastened to a motor shaft of a drive motor, which is received in the optical unit and not visible in FIG. 6, are shown, the gearwheel meshing with an internally toothed ring gear (not depicted here) securely connected to the external housing 4 of the exoscope 1 and serving to rotate the optical unit 11 about the axis of rotation 28 thereof (see also FIGS. 1*a*, 1*b*, 4*a*, 4*b*). Furthermore, a laser pointer 66 serving as a marker light source is illustrated.

Figure 7:
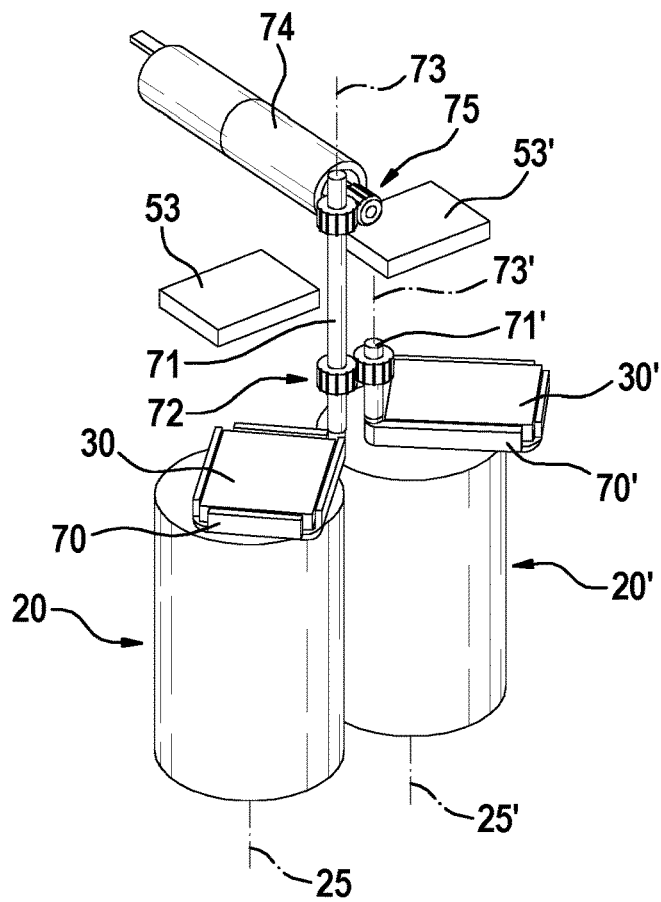
FIG. 7 shows selected optical elements of an optical unit in accordance with a second exemplary embodiment of the invention in a simplified illustration.

FIG. 7 shows selected optical elements of the observation optical unit in accordance with a further embodiment of the invention in an illustration corresponding to that of FIG. 4*b*. A filter 30, 30' is swiveled-in between the objective 20, 20' and the image sensor 53, 53' of both stereo channels in each case. For carrying out the swivel movement, the filters 30, 30' are each received in a filter carrier 70, 70', which filter carriers are fastened to a filter shaft 71, 71' in each case. The filter shaft 71' of the filter carrier 70' of the second stereo channel is driven by the filter shaft 71 of the filter carrier 70 of the first stereo channel by way of a gearing 72 depicted symbolically in FIG. 7. The filter shaft 71 is driven by way of an electric motor 74 by means of a gearing 75 likewise depicted symbolically. The filter shafts 71, 71' in each case define a swivel axis 73, 73' of the filter 30, 30'. The swivel axes 73, 73' are directed parallel to the optical axes 25, 25' of the objectives 20, 20' and extend between the objectives 20, 20' or in a region closely adjacent to the axis of rotation, which corresponds to a center line between the optical axes 25, 25'; as is shown in FIG. 7, the swivel axis 73, for example, can be identical to the axis of rotation which extends in FIG. 7 in a manner corresponding to that of FIGS. 4*a* and 4*b*. What this achieves is that the filters 30, 30' can be swiveled from the position swiveled into the beam paths of the stereo channels, as shown in FIG. 7, into a swiveled-out position, which is arranged next to the beam paths of the stereo channels, i.e. into a spatial region in front of the objectives 20, 20' or offset upward in the illustration of FIG. 7. What can be achieved by an axially offset arrangement of the filter carriers 70, 70' is that both filter carriers 70, 70' can be swiveled to the same side of the beam paths, i.e. in the spatial region in front of the objectives 20, 20'. Otherwise, the exemplary embodiment depicted in FIG. 7 can be embodied as described in relation to FIGS. 1 to 6.

For reasons of clarity, all reference signs are not depicted in all figures. Reference signs not explained in relation to one figure have the same meaning as in the remaining figures.

The invention being thus described, it will be obvious that the same may be varied in many ways. Such variations are not to be regarded as a departure from the spirit and scope of the invention, and all such modifications as would be obvious to one skilled in the art are to be included within the scope of the following claims.

What is claimed is:

1. An apparatus for recording an image of an object field on a body from outside of the body, the apparatus comprising:
    a shank; and
    an optical unit arranged at a distal end of the shank, the optical unit comprising an observation optical unit for recording the image of the object field and being rotatable about an axis of rotation that is at least substantially parallel to a viewing direction of the observation optical unit,
    wherein the observation optical unit has a first stereo channel and a second stereo channel, the first and second stereo channels having an objective and at least one electronic image recorder,
    wherein the observation optical unit comprises at least one filter that is swivelable into a beam path of the observation optical unit and swivelable therefrom, and
    wherein the at least one filter is swivelable about a swivel axis formed substantially perpendicular to the axis of rotation.

2. The apparatus as claimed in claim 1, wherein an optical axis of the objective in the first stereo channel and an optical axis of the objective in the second stereo channel lie in a common plane and wherein the swivel axis lies at least substantially in the common plane or in a plane substantially parallel thereto.

3. The apparatus as claimed in claim 1, wherein the at least one filter comprises a first filter and a second filter, wherein the first filter is swivelable into a beam path of the first stereo channel and swivelable therefrom, and the second filter is swivelable into a beam path of the second stereo channel and swivelable therefrom.

4. The apparatus as claimed in claim 3, wherein the first filter is swivelable in and out between the objective and the at least one image recorder of the first stereo channel, and the second filter is swivelable in and out between the objective and the at least one image recorder of the second stereo channel.

5. The apparatus as claimed in claim 4, wherein the first filter and the second filter are arranged on a common swivelable filter carrier.

6. The apparatus as claimed in claim 3, wherein the first filter and the second filter have substantially the same spectral characteristics.

7. The apparatus as claimed in claim 3, wherein the first filter and the second filter have different spectral characteristics.

8. The apparatus as claimed in claim 1, wherein the at least one filter is swivelable via a motor.

9. The apparatus as claimed in claim 1, wherein the optical unit comprises at least one sensor for detecting a swivel position of the at least one filter.

10. The apparatus as claimed in claim 9, wherein the at least one sensor is a magnetic sensor and/or a proximity switch.

11. The apparatus as claimed in claim 1, wherein the observation optical unit comprises a focusing device.

12. The apparatus as claimed in claim 1, wherein the optical unit comprises a marker light source.

13. The apparatus as claimed in claim 1, wherein the first stereo channel and the second stereo channel each comprise at least one further electronic image recorder and a beam splitter.

14. The apparatus as claimed in claim 1, wherein the optical unit has a hermetically sealed embodiment.

15. The apparatus as claimed in claim 1, wherein the body is a human body or animal body.

16. The apparatus as claimed in claim 1, further comprising an external housing that is stationarily attached to the distal end of the shank, wherein the optical unit is accommodated inside of the external housing, and wherein the observation optical unit rotates within the external housing about the axis of rotation.

17. The apparatus as claimed in claim 16, wherein the axis of rotation of the observation optical unit is perpendicular to the axis of the shank.

18. The apparatus as claimed in claim 16, wherein the optical unit includes a housing and a base plate that closes the housing, wherein the objective and the at least one electronic image recorder of the first and second stereo channels are positioned inside of the housing of the optical unit.

19. The apparatus as claimed in claim 11, wherein the focusing device includes a carriage and a sliding guide that extends parallel to the axis of rotation of the observation optical unit, wherein the objectives of the first stereo channel and the second stereo channel are attached to the carriage, the carriage being slidable along an axial direction of the sliding guide.

20. An apparatus for recording an image of an object field on a body from outside of the body, the apparatus comprising:
- a shank; and
- an optical unit arranged at a distal end of the shank, the optical unit comprising an observation optical unit for recording the image of the object field and being rotatable about an axis of rotation that is at least substantially parallel to a viewing direction of the observation optical unit,
- wherein the observation optical unit has a first stereo channel and a second stereo channel, the first and second stereo channels having an objective and at least one electronic image recorder,
- wherein the observation optical unit comprises at least one filter that is swivelable into a beam path of the observation optical unit and swivelable therefrom, and
- wherein the at least one filter includes a first filter and a second filter that are each simultaneously swivelable into a beam path of the observation optical unit and swivelable therefrom into a spatial region arranged laterally with respect to the beam paths of both the first and second stereo channels.

21. The apparatus as claimed in claim 20, wherein the first filter is attached to a first filter shaft, the first filter shaft being swivelable about a first swivel axis and the second filter is attached to a second filter shaft, the second filter shaft being swivelable about a second swivel axis,
- wherein the first swivel axis is aligned with the axis of rotation of the observation optical unit and the second swivel axis is substantially parallel to the first swivel axis, and
- wherein a gear provided on the first filter shaft engages with a gear provided on the second filter shaft, such that rotation of the first filter shaft causes rotation of the second filter shaft.

* * * * *